US006280657B1

(12) United States Patent
McEntee

(10) Patent No.: US 6,280,657 B1
(45) Date of Patent: Aug. 28, 2001

(54) KETOXIME SOLUTIONS OF BIOCIDES

(75) Inventor: Thomas C. McEntee, Topsfield, MA (US)

(73) Assignee: Rohm and Haas Company, Phila, PA (US)

( * ) Notice: Subject to any disclaimer, the term of this patent is extended or adjusted under 35 U.S.C. 154(b) by 0 days.

(21) Appl. No.: 09/085,806

(22) Filed: May 27, 1998

(51) Int. Cl.$^7$ .......................... C09K 15/20; A01N 25/02

(52) U.S. Cl. .................. 252/400.31; 252/405; 424/405; 424/409

(58) Field of Search .............................. 252/400.31, 405; 424/405, 409

(56) References Cited

U.S. PATENT DOCUMENTS

| | | | | |
|---|---|---|---|---|
| 3,189,576 | | 6/1965 | Sweet | 260/46.5 |
| 3,947,576 | * | 3/1976 | Kuczkowski et al. | 514/347 |
| 4,034,097 | * | 7/1977 | Kuczkowski et al. | 514/347 |
| 4,711,914 | | 12/1987 | Rei et al. | 523/122 |
| 4,761,247 | | 8/1988 | Rei et al. | 252/364 |
| 4,808,212 | * | 2/1989 | Plath et al. | 504/247 |
| 4,891,391 | | 1/1990 | McEntee | 523/122 |
| 5,026,875 | * | 6/1991 | Takeda et al. | 549/201 |
| 5,498,344 | | 3/1996 | Rei et al. | 252/404 |
| 5,554,635 | | 9/1996 | Rei et al. | 514/372 |
| 5,559,083 | * | 9/1996 | Kubota et al. | 504/269 |
| 5,712,275 | * | 1/1998 | Van Gestel | 514/222.5 |

* cited by examiner

*Primary Examiner*—Jill Warden
*Assistant Examiner*—LaToya I Cross
(74) *Attorney, Agent, or Firm*—Jeffrey H. Rosedale

(57) ABSTRACT

Concentrated solutions of biocides are provided, particularly for silicone caulks, which comprise a biocide, sufficient levels of a ketoxime as a solvent for the biocide, and optional non-volatile carrier liquid.

13 Claims, No Drawings

KETOXIME SOLUTIONS OF BIOCIDES

The present invention is directed to biocide solutions particularly suitable for addition to silicone caulks.

BACKGROUND OF THE INVENTION

A variety of products contain biocides to prevent their pre-mature degradation caused by microbial growth and/or to prevent unsightly appearance caused by microbial staining. Important biocides, and biocides of particular interest herein, are phenoxarsines and phenarsazines, 10,10'-oxybisphenoxarsine (OBPA) being of particular interest, and isothiazolinones, 4,5 dichloro-2-n-octyl-4-isothiazol-3-one and 2-n-octyl-4-isothiazol-3-one being of particular interest.

For ease of handling, e.g., to prevent powdered materials from diffusing into the air and creating hazardous conditions at the workplace, many biocides are packaged as concentrates. Liquid concentrates typically comprise a biocide and a solvent for a biocide, and very often contain an additional functional component, such as a plasticizer, when the biocide concentrate is to be incorporated in a plastic composition. Examples of liquid biocide concentrates are found in U.S. Pat. Nos. 4,711,914, 4,761,247, 4,891,391, and 5,498,344, the teaching of each of which are incorporated herein by reference.

Among products to which biocides are commonly added are silicone caulks. The term "caulk" is used herein broadly to include silicone elastomers useful as sealants, adhesives, etc. Most commercial silicone caulks are based on silanol-terminated polydimethyl siloxanes, although the pendant groups may be, to a greater or lesser extent, other than methyl, e.g., phenyl, cyanoethyl or trifluoropropyl. Tri- and tetra-functional silanes serve as cross-linking agents, the functional organic groups of such silanes being, for example, alcohols, carboxylic acids, amines, ketoximines, aldoximes, and amides. Acetic acid, is the most common functional group of cross-linking silanes; dissociation of the acetic acid group from the silane during curing being responsible for the vinegar smell associated with many such caulks. Accordingly, where odor is of concern, silanes with other functional groups, such as ketoximes (e.g., methylethylketoxime) are used. Caulks generally contain fillers, such as silica. In two-part caulks, a condensation catalyst, such as a tin soap, is contained in a part separate from the polysiloxane. One-part caulks are produced in entirely anhydrous conditions and rely on diffusion of moisture from the air to effect a cure. One-part caulks may rely entirely on moisture to effect a cure, but in some cases may contain a condensation catalyst. Both two-part and one-part silicone caulks undergo room temperature vulcanization (RTV).

Currently, a biocide concentrate for silicone caulks comprises OBPA as the biocide, nonylphenol as the solvent, and a silicone oil, particularly poly(dimethyl siloxane). The poly(dimethyl siloxane) acts to compatibilize the biocide with the polysiloxane of the caulking composition to which it is added. Some silicone caulk producers use a composition comprising OBPA, isodecanol and the plasticizer di-(2-ethyl hexyl) phthalate. 2-ethyl-1,3-hexanediol has also been used as an OBPA solvent in silicone caulks. In such compositions, the solvents and any plasticizer are non-volatile and remain in the silicone caulk as it cures. The solvents and di-(2-ethyl hexyl), however, are viewed as adulterants, having uncertain effects on the final product. Nonylphenol yellows some compounds upon exposure to sunlight.

Many biocides, such as OBPA 4,5 dichloro-2-n-octyl-4-isothiazol-3-one and, 2-n-octyl-4-isothiazol-3-one have low solubility in many organic solvents. Furthermore, selection of appropriate solvents is complicated because (1) the solvent cannot interfere with the RTV reaction; (2) the oligomers used in the caulk are somewhat viscous (3) the aesthetic properties of the caulk, such as color and odor are important, and (4) there are many formulators of proprietary caulk formulas with a wide range of formulas to satisfy different physical property requirements such as flexibility, white-pigmented, adhesion to glass, metal, etc. It has proven difficult to find a solvent for anti-microbials that does not detract from one or another desired attribute discussed above. Also, it is not common in the silicone caulk industry to add volatile compounds, with the exception of the functional groups of the silane which volatalize during the room temperature vulcanization.

SUMMARY OF THE INVENTION

In accordance with one aspect of the invention, there is provided a concentrate of a biocide in a ketoxime having the formula $C_{1-3}$alkyl—C(=N—OH)—$C_{1-3}$alkyl. The biocide is present at at least about 1 wt %, preferably between about 5 and about 10 wt %, up to the limit of solubility of the biocide in the ketoxime; the ketoxime being present in sufficient quantity to dissolve the biocide, up to the balance of the concentrate. The preferred ketoxime is methylethylketoxime (MEKO).

In accordance with another aspect of the invention a concentrate comprises at least about 1 wt %, preferably between about 5 and about 10 wt % of a biocide, between about 30 and about 70% of a functional liquid carrier, plus sufficient ketoxime having the formula $C_{1-3}$—C(=N—OH)—$C_{1-3}$ to dissolve the biocide, up to the balance of the composition.

DETAILED DESCRIPTION OF CERTAIN PREFERRED EMBODIMENTS

Herein it is surprisingly found that ketoximes are good solvents for hard-to-dissolve biocides, such as OBPA, 4,5 dichloro-2-n-octyl-4-isothiazol-3-one (DCOIT), 2-n-octyl-4-isothiazol-3-one (OIT), and 5-chloro-2-(2,4-dichlorophenoxy) phenol (TCCP). MEKO as a solvent for DCOIT is especially valuable as this biocide is poorly soluble in propylene glycol, a commonly used solvent for biocide concentrates. TCCP is not soluble in typical silicone oils, but through the use of the ketoxime can be introduced into silicone fluids. From a commercial availability standpoint, MEKO is the currently preferred ketoxime. Also, because MEKO is a known functional group of silane crosslinking agents used in silicone caulks, its compatibility with such systems is known. As such, ketoximes as biocide solvents should be readily acceptable to the industry. Other ketoximes of the above-formula are also suitable.

Isothiazolinones are generally soluble in MEKO. MEKO is most advantageous for dissolving isothiazolinones which are difficult to dissolve in water or other solvents. Additional specific isothiazolinones which may be dissolved in MEKO include, but are not limited to 4,5-dichloro-2-cyclohexyl-3-isothiazolinone (CHXIT), 5-chloro-2-methyl-4-isothiazolin-3-one, and 2-methyl-4-isothiazolin-3-one. Of the phenoxarsines, OBPA is of most commercial interest.

The best economy of materials is achieved with a relatively concentrated biocide product which minimizes the amount of the ketoxime solvent used to formulate the silicone compound. However, for mixing efficiency, it is preferable to introduce low-addition level performance additives, such as biocides, in the presence of bulkier component(s), (represented by the ketoxime and optional cosolvent). This is particularly advantageous when the composition is difficult to mix, which is a property of caulks and the silicone polymers that are used to compound the composition.

Therefore, the preferred composition of the invention will be a balance of (1) high concentration for economy of solvent usage (2) optimal match of mixing equipment and requirements over a range of viscosities, and (3) the optimum use level of biocide to achieve the level of performance in the service-life of the silicone caulk. Much of the literature shows that the biocide use levels are from 0.01 wt % to 0.5 wt % with 0.05–0.1 wt % being most common. A satisfactory mixing ratio for normal equipment is 1 part biocide concentrate to 99 parts silicone caulk components. Taking these factors into consideration, a generally useful concentrate will contain between about 5 and about 10 wt % biocide active ingredient.

The ketoxime must be present at a sufficient amount to dissolve the biocide. The amount of ketoxime necessary will depend upon the particular biocide or biocides in the concentrate, the level of biocide use, the particular ketoxime, physical stability of the solution over a range of temperatures, as well as the presence or absence of any additional functional carrier liquid. Generally, however, compositions in accordance with the invention will contain at least about 10 wt % of the ketoxime, and preferably the minimum level of ketoxime required to maintain a stable solution until the concentrate is used. Beyond this, the ketoxime may comprise the balance of the solvent or may be admixed with other organic solvents which are compatible with the biocide, the ketoxime, and the end-use product to which the concentrate is added. Suitable co-solvents include, but are not limited to phthalate plasticizers or polyols, and silicon oils or resins. It is generally preferred, however, that the ketoxime be the only volatile solvent in the composition.

While a concentrate may contain only the biocide and the ketoxime (alone or with co-solvents), in many cases it is preferred to include a functional carrier liquid. As opposed, to the ketoxime and any other volatile co-solvents, such functional carrier liquids are non-volatile and are intended to remain as a functional component incorporated in the end-use product. For addition to silicone caulks, preferred carrier liquids are silicone oils, such as poly(dimethyl siloxane), which compatibilize the biocide concentrate with the silicone caulk to which it is to be added. Beyond the desired level of biocides in such concentrates, and such amount of ketoxime necessary to dissolve the biocide and maintain the biocide in stable solution, the inclusion of significant amounts of a functional carrier liquid is desirable from the standpoint of providing a second useful component in the concentrate and reducing the amount of the the ketoxime. While the ketoxime is fully compatible with silicone caulks and is substantially odorless, it nevertheless represents a volatile organic component; thus, its use at as low a level consistent with a stable concentrate is desired.

While the compositions of the present invention are particularly desirable for silicone caulks and similar silicone compositions, concentrates in accordance with the invention may be used in other applications where liquid biocide concentrates are typically employed, such as in flexible polyvinyl chloride compositions. In such, the functional carrier liquid may be adapted for the particular purpose, such as a plasticizer for flexible polyvinyl chloride. Some suitable plasticizers include, but are not limited to di-2-ethyl hexyl phthalate, diisodecyl phthalate, butyl benzyl phthalate, and epoxidized soya. Other suitable plasticizers are described, for example, in U.S. Pat. No. 5,554,635, the teachings of which are incorporated herein by reference.

A further advantage of the use of ketoximes as biocide solvents in the silicone caulk area is the achievement of clearer compositions. To further clarify the caulks, poly (ethylene glycol) may be used as a non-volatile liquid carrier.

The invention will now be described in greater detail by way of specific examples.

EXAMPLES 1–12

Concentrates of OBPA, DCOIT and OIT in MEKO were formulated as per Table 1 below.

TABLE 1

Solubility/Stability of Biocides in MEKO . . . Experimental Formulations (% by weight)

| | OBPA Series | | | DCOIT Series | | | | | OIT Series | | | |
| --- | --- | --- | --- | --- | --- | --- | --- | --- | --- | --- | --- | --- |
| | 1 | 2 | 3 | 4 | 5 | 6 | 7 | 8 | 9 | 10 | 11 | 12 |
| MEKO | 98 | 95 | 90 | 90 | 90 | 80 | 60 | 40 | 90 | 80 | 60 | 40 |
| OBPA | 2 | 5 | 10 | | | | | | | | | |
| DCOIT | | | | 10 | 10 | 20 | 40 | 60 | | | | |
| OIT | | | | | | | | | 10 | 20 | 40 | 60 |
| Formulating Temperature | 285° F. | | | 285° F. | Room Temperature | | | | 285° F. | Room Temperature | | |

One sample (25–50g) was prepared for each formulation listed in table 1. The components for formulations #1–4 & 9 were placed in a beaker, warmed to 285° F (141° C.) and held for 5-minutes while mixing. These formulations were then transferred to 8-dram glass vials for storage. The components for the formulations prepared at room temperature (#5–8, 10–12) were placed in an 8-dram glass vial and shaken until the biocide dissolved. The samples were stored at room temperature and visually examined for evidence of separation, crystal formation or other unusual characteristic. The samples were prepared over a 12-day period and therefore, the storage time varies.

Results are shown in Table 2 below:

TABLE 2

| Solubility/Stability of Biocides in MEKO . . . Appearance (% by weight) | | | | | | | | | | | | |
|---|---|---|---|---|---|---|---|---|---|---|---|---|
| | OBPA Series | | | DCOIT Series | | | | | OIT Series | | | |
| | 1 | 2 | 3 | 4 | 5 | 6 | 7 | 8 | 9 | 10 | 11 | 12 |
| MEKO | 98 | 95 | 90 | 90 | 90 | 80 | 60 | 40 | 90 | 80 | 60 | 40 |
| OBPA | 2 | 5 | 10 | | | | | | | | | |
| DCOIT | | | | 10 | 10 | 20 | 40 | 60 | | | | |
| OIT | | | | | | | | | 10 | 20 | 40 | 60 |
| Days Stored | 30 | 30 | 42 | 42 | 42 | 38 | 38 | 30 | 42 | 38 | 38 | 30 |
| Appearance | A slight amount of a white, powder like substance was present in formulation 1 & 2 Crystals were present in formulation 3 after 3-days of storage | | | A slight amount of a white, powder like substance was present in formulations 4–7. The DCOIT did not completely dissolve in formulation 8. | | | | | A slight amount of white powder like substance was present in all the samples. No liquid separation or crystal formation was noted. | | | |

A slight amount of a white, powder like substance formed in all the formulations. It is uncertain whether this substance is from an impurity in the biocide or the result of an interaction between the biocide and MEKO.

EXAMPLES 13–15

A 30-day study was conducted with Vinyzene® DP-7000/ MEKO formulations.

Solutions of TCCP in MEKO were formulated as per Table 3 below:

TABLE 3

| Solution Stability of TCPP in MEKO . . . Formulations (weight %) | | | |
|---|---|---|---|
| | 13 | 14 | 15 |
| MEKO | 95.0 | 90.0 | 80.0 |
| TCPP | 5.0 | 10.0 | 20.0 |

100 g of each formulation listed in table 1 were prepared. The components were added to a beaker and mixed until all the DP-7000 appeared to be dissolved. The solutions were then heated to 100° F. (37.8° C.) and held for 10-minutes. Each formulation was transferred to four 8-dram glass vials for stability testing as follows:

Shelf, Warehouse and Freezer Stability Testing

For each formulation, one tightly sealed 8-dram vial containing the formulated product was placed on a shelf at room temperature, in an oven set at 140° F. (60° C.) and in a freezer set at 14° F. (−10° C.). The samples were visually examined after 30 days of storage for evidence of separation, color development and/or crystal formation.

Freeze/Thaw Testing

For each formulation, one tightly sealed 8-dram vial containing the formulated product was subjected to five freeze/thaw cycles. A cycle consisted of 2 to 4-days at 14° F. (−10° C.) followed by 1-day at room temperature. The samples were visually examined after each cycle for evidence of separation, color development and/or crystal formation.

Results are shown in Tables 4 and 5 below:

TABLE 4

| Solution Stability of DP-7000/MEKO Formulations . . . 30-day Observations | | | | |
|---|---|---|---|---|
| | Form | Room Temp | Initial −10° C. | 30-days at . . . 60° C. |
| 13 | Clear Water White | Slightly yellowed Otherwise, clear with no evidence of separation or crystal formation | Samples didn't freeze Clear, water white No evidence of separation, color development or crystal formation | Clear, water white No evidence of separation, color development or crystal formation |
| 14 | Clear Water White | Slightly yellowed Otherwise, clear with no evidence of separation or crystal formation | Samples didn't freeze Clear, water white No evidence of separation, color development or crystal formation | Clear, water white No evidence of separation, color development or crystal formation |
| 15 | Clear Water White | Slightly yellowed Otherwise, clear with no evidence of separation or crystal formation | Samples didn't freeze Clear, water white No evidence of separation, color development or crystal formation | Clear, water white No evidence of separation, color development or crystal formation |

TABLE 5

Solution Stability of DP-7000/MEKO Formulations . . . Freeze/Thaw Observations

| Form. | Freeze/Thaw Stability | | | | |
|---|---|---|---|---|---|
| | Cycle 1 | Cycle 2 | Cycle 3 | Cycle 4 | Cycle 5 |
| 13 | Samples didn't freeze. No evidence of separation, color development, crystal formation or other unusual characteristic | Samples didn't freeze. No evidence of separation, color development, crystal formation or other unusual characteristic | Samples didn't freeze. No evidence of separation, color development, crystal formation or other unusual characteristic | Samples didn't freeze. No evidence of separation, color development, crystal formation or other unusual characteristic | Samples didn't freeze. No evidence of separation, color development, crystal formation or other unusual characteristic |
| 14 | Samples didn't freeze. No evidence of separation, color development, crystal formation or other unusual characteristic | Samples didn't freeze. No evidence of separation, color development, crystal formation or other unusual characteristic | Samples didn't freeze. No evidence of separation, color development, crystal formation or other unusual characteristic | Samples didn't freeze. No evidence of separation, color development, crystal formation or other unusual characteristic | Samples didn't freeze. No evidence of separation, color development, crystal formation or other unusual characteristic |
| 15 | Samples didn't freeze. No evidence of separation, color development, crystal formation or other unusual characteristic | Samples didn't freeze. No evidence of separation, color development, crystal formation or other unusual characteristic | Samples didn't freeze. No evidence of separation, color dcvelopment, crystal formation or other unusual characteristic | Samples didn't freeze. No evidence of separation, color development, crystal formation or other unusual characteristic | Samples didn't freeze. No evidence of separation, color development, crystal formation or other unusual characteristic |

Thus, formulations containing up to 20% DP-7000 (TCPP) in MEKO exhibited excellent solution stability when stored under ambient and adverse conditions. A slight color development occurred in the formulations stored at room temperature.

What is claimed is:

1. A composition, comprising:

at least 1 wt % of a biocide, at least 10 wt % of a ketoxime having the formula $C_{1-3}$alkyl—C(═N—OH)—$C_{1-3}$alkyl to dissolve said biocide, and between 30 wt % and 70 wt % of a non-volatile carrier liquid.

2. The composition according to claim 1 wherein said ketoxime is methylethylketoxime.

3. The composition according to claim 1 wherein said non-volatile carrier liquid is a silicone oil.

4. The composition according to claim 3 wherein said silicone oil is poly (dimethyl siloxane).

5. The composition according to claim 1 wherein said non-volatile carrier liquid is a plasticizer.

6. The composition according to claim 1 wherein said non-volatile carrier liquid is poly (ethylene glycol).

7. A composition, comprising:

at least 1 wt % of a biocide, said biocide selected from the group consisting of phenoxarsines, phenarsazines, and isothiazolinones, and at least 10 wt % of a ketoxime having the formula $C_{1-3}$alkyl—C(═N—OH)—$C_{1-3}$alkyl to dissolve said biocide and a non-volatile carrier liquid.

8. The composition according to claim 7 wherein said biocide comprises 10, 10'-oxybisphenoxarsine.

9. The composition according to claim 7 wherein said biocide comprises 4,5 dichloro-2-n-octyl-4-isothiazol-3-one.

10. The composition according to claim 7 wherein said biocide comprises 2n-octyl-4-isothiazol-3-one.

11. The composition according to claim 7 wherein said biocide comprises 4,5-dichloro-2-cyclohexyl-3-isothiazolinone.

12. The composition according to claim 7 wherein said composition comprises said biocide and said non-volatile carrier liquid, the balance of said composition being said ketoxime.

13. A composition, comprising:

at least 1 wt % of a biocide, said biocide comprising 5-chloro-2-(2,4-dichlorophenoxy)phenol, and at least 10 wt % of a ketoxime having the formula $C_{1-3}$alkyl—C(═N—OH)—$C_{1-3}$alkyl to dissolve said biocide and a non-volatile carrier liquid.

* * * * *